United States Patent [19]
Ootani et al.

[11] Patent Number: 5,384,093
[45] Date of Patent: Jan. 24, 1995

[54] APPARATUS FOR ASPIRATING AND DISCHARGING A LIQUID SAMPLE

[75] Inventors: Toshihiro Ootani; Takayoshi Izumi, both of Kobe, Japan

[73] Assignee: Toa Medical Electronics Co., Ltd., Kobe, Japan

[21] Appl. No.: 35,400

[22] Filed: Mar. 23, 1993

[30] Foreign Application Priority Data

Apr. 3, 1992 [JP] Japan .................. 4-029020[U]

[51] Int. Cl.6 ........................................... G01N 33/00
[52] U.S. Cl. ............................................ 422/63; 422/65; 422/100; 422/104; 436/43; 436/47; 436/48; 436/49
[58] Field of Search .................. 422/63, 65, 66, 99, 422/104, 100; 436/43, 47, 48, 49, 807

[56] References Cited

U.S. PATENT DOCUMENTS

| | | | |
|---|---|---|---|
| 4,582,990 | 4/1986 | Stevens | 250/328 |
| 4,803,050 | 2/1989 | Mack | 422/65 |
| 5,055,263 | 10/1991 | Meltzer | 422/65 |
| 5,055,408 | 10/1991 | Higo et al. | 436/48 |
| 5,096,670 | 3/1992 | Harris et al. | 422/65 |
| 5,104,621 | 4/1992 | Pfost et al. | 422/67 |
| 5,158,895 | 10/1992 | Ashihara et al. | 436/526 |
| 5,206,171 | 4/1993 | Dillon et al. | 435/293 |
| 5,232,665 | 8/1993 | Burkovich et al. | 422/65 |
| 5,260,028 | 11/1993 | Astle | 422/81 |
| 5,270,006 | 12/1993 | Uchigaki et al. | 422/63 |

*Primary Examiner*—James C. Housel
*Assistant Examiner*—Long H. Le
*Attorney, Agent, or Firm*—Jones, Tullar & Cooper

[57] ABSTRACT

An apparatus for aspirating and discharging a specific volume of liquid sample, such as specimen and reagent, has a reaction plate serving a holding function and having a plurality of reaction containers, is provided which is low in cost and compact in design. On one side of a belt applied on two pulleys driven by one driving source an arm for holding a pipet is provided, while a reaction plate holding part is mounted on the other side of the belt (112), thereby constructing an apparatus for aspirating and discharging a liquid sample. When the arm ascends, the holding part descends, and when the arm descends, the holding part ascends. Thus, the arm and holding part are moved mutually in opposite directions by one driving source.

2 Claims, 9 Drawing Sheets

5,384,093

APPARATUS FOR ASPIRATING AND DISCHARGING A LIQUID SAMPLE

BACKGROUND OF THE INVENTION

The present invention relates to an apparatus for aspirating and discharging a specific volume of a liquid sample such as specimen and reagent. More particularly, the present invention relates to an apparatus for aspirating and discharging a liquid sample which is of low cost and compact design possessing a reaction plate holding mechanism having a plurality of reaction containers.

A sample analyzer using a reaction plate having a plurality of reaction containers provided on one plate is known. Such an apparatus is designed to distribute specimen, buffer solution, reagent, etc. to the containers of the reaction plate that has been set, cause specific reactions in the containers, and measure the characteristic of reaction liquids in the measuring unit.

In the sample analyzer using the reaction plate, means aspirating and discharging liquid sample that is movable two-dimensionally is required. Also, the holding and moving means of the reaction plate is also needed. They too are individually known.

It is therefore very advantageous for cost and size if the function for two-dimensional moving and the function for holding and moving the reaction plate can be assembled into one compact structure.

OBJECT AND SUMMARY OF THE INVENTION

It is hence a primary object of the present invention to provide an apparatus for aspirating and discharging a liquid sample possessing a reaction plate holding mechanism and one capable of two-dimensional movement.

To achieve the above object, the present invention presents an apparatus for aspirating and discharging a liquid sample comprising:
- a pipet for aspirating and discharging a liquid sample,
- an arm 82 for drooping and holding the pipet 82,
- guide means for moving the arm in the vertical direction,
- a reaction plate holding part for holding a reaction plate possessing a plurality of reaction containers,
- guide means for moving the reaction plate holding part in the vertical direction,
- a pair of pulleys,
- a belt applied on the pulleys having the arm attached to one side of the belt and the reaction plate holding part on the another side of the belt, and
- a driving source for rotating the belt.

That is, the arm and the reaction plate holding part are installed on the opposite sides of the belt.

The apparatus for aspirating and discharging a liquid sample is assembled in an XY moving part 70 which is movable two-dimensionally.

By the operation of the driving source, the belt applied on the pulleys is put in rotation. The arm and the reaction plate holding part are mounted on the opposite sides of the belt, and therefore the arm and the holding part move mutually in reverse directions. That is, when the arm ascends, the holding part descends, and when the arm descends, the holding part ascends.

Accordingly, when the holding part is lowered for holding the reaction plate (or releasing the held reaction plate), the pipet ascends, and there is no obstacle for the holding (or releasing) of the reaction plate. On the contrary, when the pipet is lowered for aspirating or discharging the liquid, the holding part ascends, so that there is no problem for aspirating or discharging action.

By moving the entire apparatus for aspirating and discharging a liquid sample longitudinally or laterally, the aspirated liquid can be discharged in another place, and it may be moved to other place by holding the reaction plate.

DETAILED DESCRIPTION OF THE PREFERRED EMBODIMENTS

Figure 1:
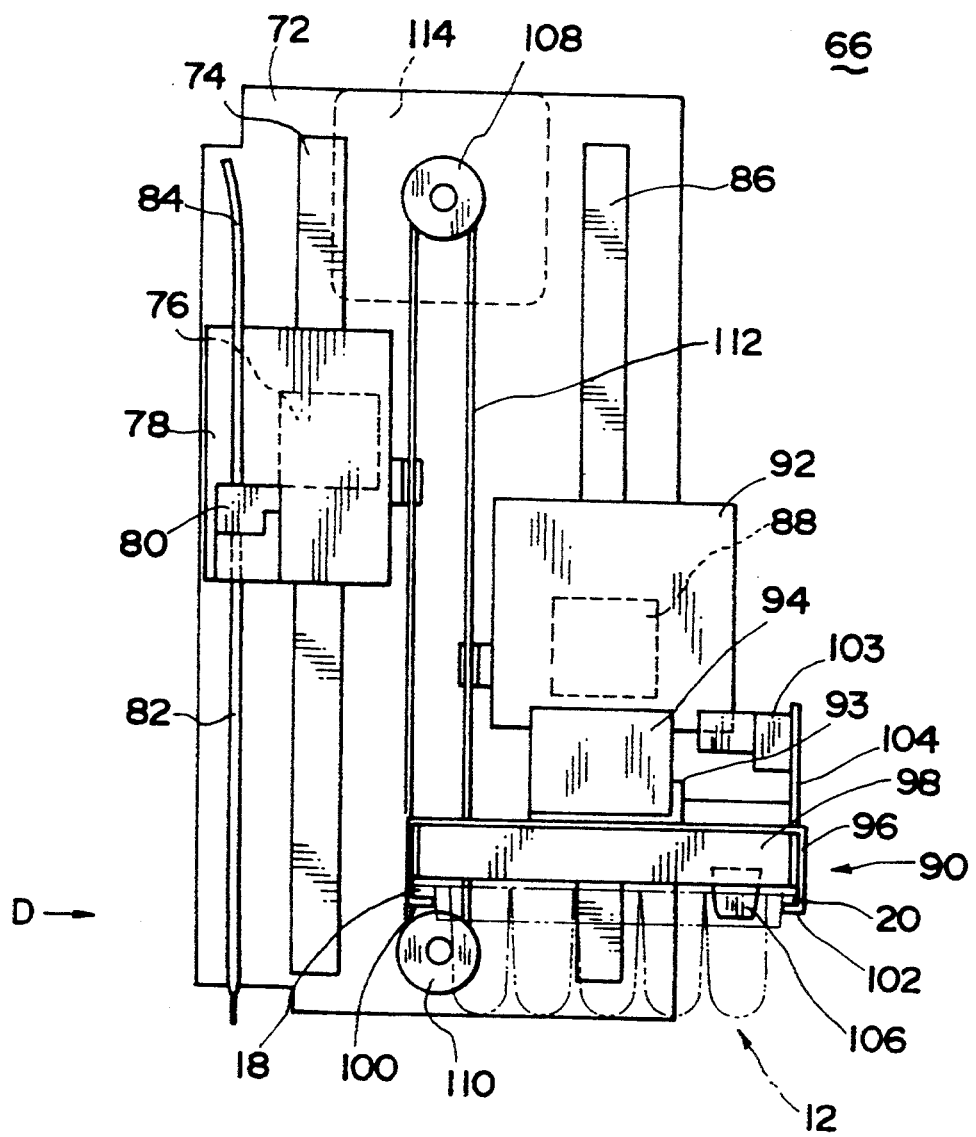
FIG. 1 is a front view showing an embodiment of an apparatus for aspirating and discharging a liquid sample of the present invention (seen from the direction of arrow C in FIG. 4).

Referring now to the drawings, some of the preferred embodiments of the present invention are described in detail below.

FIG. 1 is a front view of the portion of the apparatus 66 for aspirating and discharging a liquid sample of the present invention (a view from the direction of arrow C in FIG. 4 below). A guide rail 74 is mounted on a base plate 72. A slider 76 moves only vertically along the guide rail 74. An arm 80 is attached to the slider 76 through a mounting member 78. An aspiration pipet 82 extends downwardly from the arm 80. A tube 84 is connected to the aspiration pipet 82. Another guide rail 86 is mounted on the base plate 72 parallel to the guide plate 74, and a slider 88 moves only vertically along the guide rail 86. The slider 88 is combined with a holding part 90 for holding the reaction plate 12 through mounting members 92, 94, 93, 96. The holding part 90 comprises the mounting member 96 having ends bent inward, that is, in a shape of notching (cutting) the middle portion of the lower side of a square, and an inside member 98 provided inside of the mounting member 96. A reaction plate 12 is held as supported by handles 18, 20 of the reaction plate 12 which are fitted in the bent parts 100, 102 of the holding part 90. A positioning sensor 103 is attached to a vertical member 104.

Figure 2:
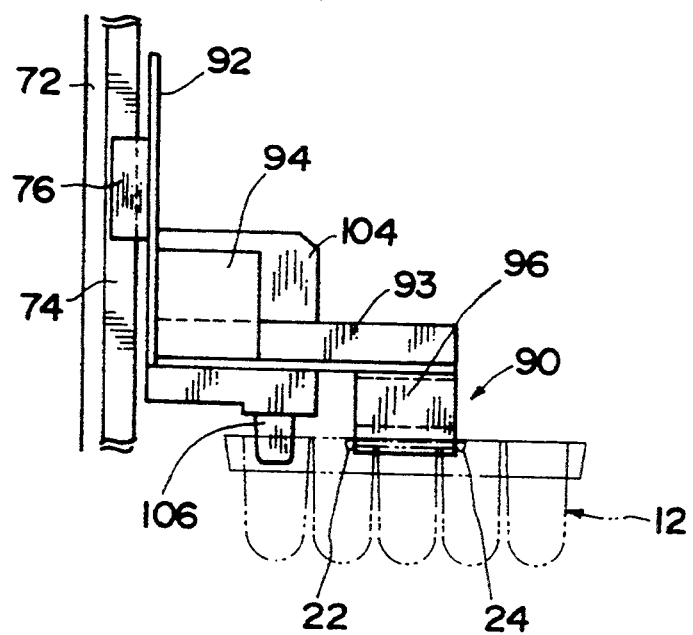
FIG. 2 is a side view of the reaction plate holding part (seen from the direction of arrow D in FIG. 1).

FIG. 2 is a view of the reaction plate holding part 90 as seen from its side (a view from direction of arrow D in FIG. 1). Since holding protrusions 22, 24 provided in the lower part at both ends of the handle 18 of the reaction plate 12 are located so as to grasp the bent part 100 from both sides, and the reaction plate 12 is lifted up while maintaining the specific position, the reaction plate doe not deviate position. Furthermore, the base plate 72 is provided with a columnar member 106 with round ends through the vertical member 104, and the columnar member 106 is designed to be fitted into one container of the reaction plate 12 when the reaction plate 12 is held and lifted by the holding part 90. Hence, the reaction plate 12 is firmly fixed, and does not deviate or loosen in spite of longitudinal or lateral movement.

The base plate 72 is rotatably provided with a pair of pulleys 108, 110, and a belt 112 is applied on the pulleys 108, 110. One pulley 108 is coupled with a rotary shaft of a motor 114, and the belt 112 can rotate both the forward and reverse direction. The mounting member 78 is connected to one side of the belt 112, while the mounting member 92 is connected to the other side of the belt 112. Hence, the arm 80 and holding part 90 move mutually in reverse directions. That is, when the arm 80 ascends, the holding part 90 descends, and when the arm 80 descends, the holding part 90 ascends. Comparing the frequency of the aspirating and discharging action of the liquid and holding action of the reaction plate, the frequency of liquid aspiration and discharge is higher by far, and it is not necessary to do both actions simultaneously, there is no problem in moving the arm 80 and holding part 90 up and down alternately by one motor 114. When the holding part 90 is lowered in order to hold the reaction plate (or release the held reaction plate), the pipet 82 goes up, and hence there is no obstacle for holding (or releasing) of the reaction plate. When the pipet 82 is lowered for aspiration or distribution of liquid, the holding part 90 goes up, and there is no problem for an aspirating and discharging action.

Figure 3:
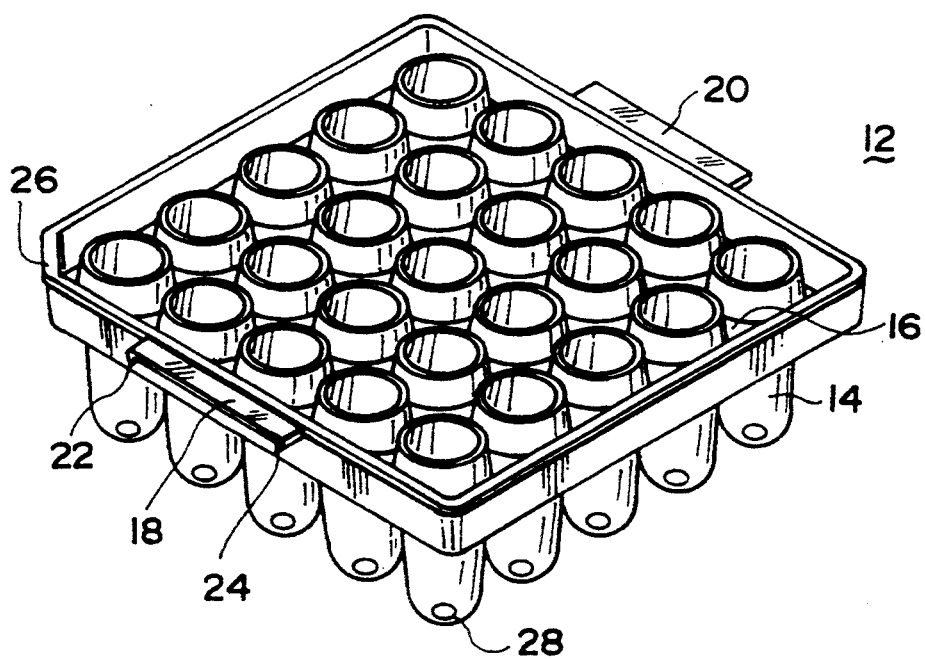
FIG. 3 is a perspective view showing an example of a reaction plate used in the apparatus of the present invention.

FIG. 3 is a perspective view of an example of a reaction plate 12 used in the apparatus of the present invention. The reaction plate 12 is made of synthetic resin, and one plate holds, for example, a total of 25 reaction containers 14 in 5 rows by 5 lines, and these containers 14 are linked with each other by a base plate 16, and all are formed in one body. The inside diameter and height of the containers 14 are, for example, about 8 mm and about 24 mm, respectively. As seen from the top, the reaction plate 12 has a square shape of one side of, for example, about 70 mm.

At both sides of the reaction plate 12, handles 18, 20 for holding the reaction plate are attached. Moreover, at both sides of the handles 18, 20, holding protrusions 22, 24 are provided, extending downwardly, so that holding of the reaction plate is much easier, while the positional deviation of the reaction plate when moving is prevented.

Structurally, the upper end and outer frame of each container 14 are located higher than the position of the base plate 16 (for example, 6 mm), and hardly any liquid in the container splashes out, and hardly liquid spilling over the base plate 16 gets into the containers 14. A corner 26 of the reaction plate 12 is partly cut for positioning purpose. In the bottom of each container 14, a recess 28 is formed. Stable dimensions are obtained in manufacture, and it is possible to securely install the apparatus. Preferably, the reaction plate is entirely made of a transparent body.

Figure 4:
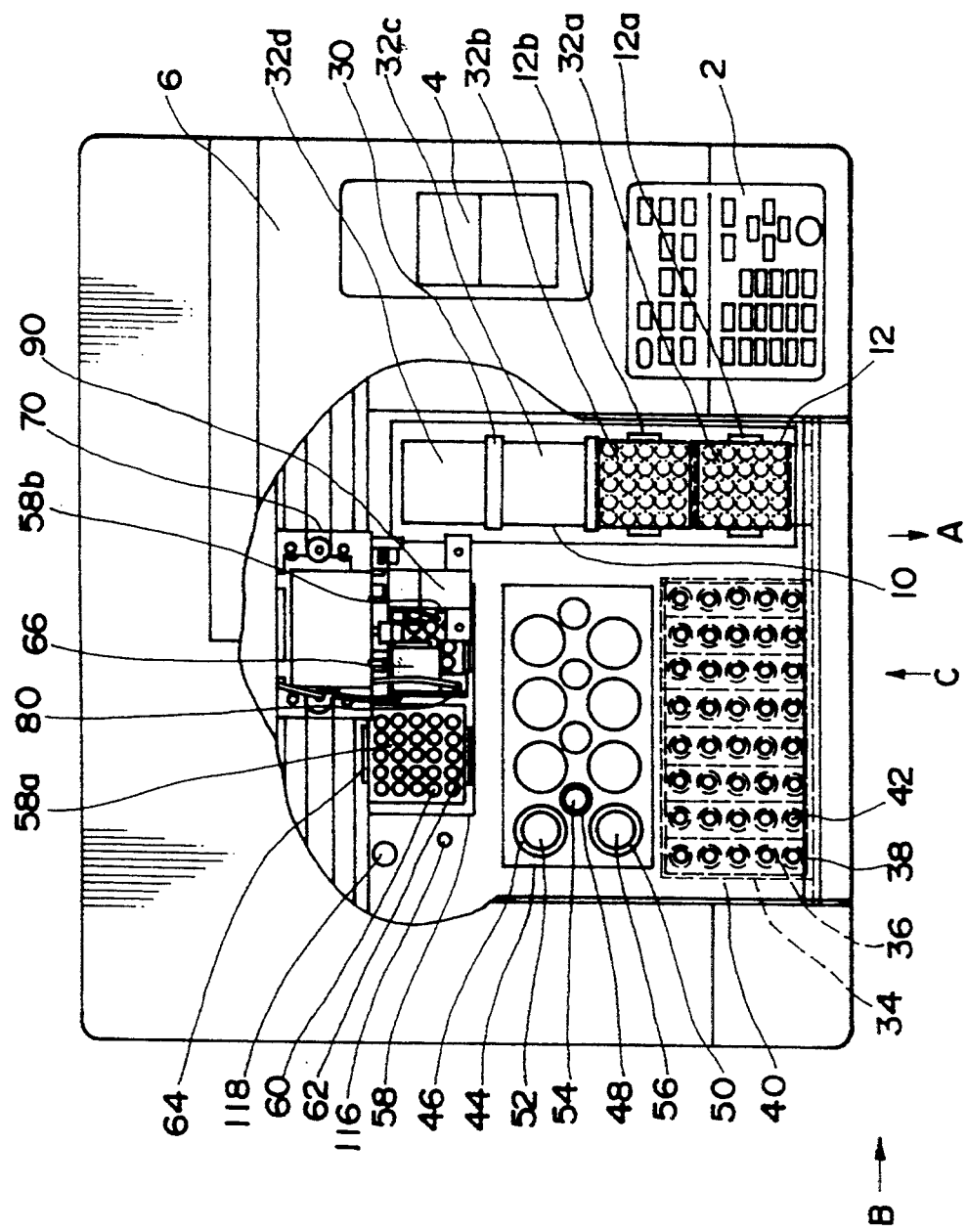
FIG. 4 is a plan view of an automated immunochemical analyzer, showing an example of the apparatus using the apparatus for aspirating and discharging a liquid sample of the present invention.

FIG. 4 is a plan view of an embodiment of an automated immunochemical analyzer showing an example of how the apparatus for aspirating and discharging a liquid sample of the present invention is used. The basic construction of the reaction system and measurement system is the same as the apparatus known hitherto. This automated immunochemical analyzer is downsized in order to reduce the cost of that conventional apparatus. A principal difference is the use of disposable reaction plates. As a result, the cleaning (rinsing) device is not needed. Besides, by using only one means for aspirating and discharging liquid, the means is moved two-dimensionally, movement of other units is eliminated, and the means is provided with a function for holding the reaction plate, so that an effective use of space and cost savings are realized.

By reference to FIG. 4, a general construction of the automated immunochemical analyzer is described below.

Numeral 10 is a table for holding reaction plates 12. Numeral 34 is a table for a specimen rack for disposing specimen racks 36. Numeral 44 is a reagent thermostatic unit for keeping reagents in a thermostatic (constant temperature) state. Numeral 58 is a reaction thermostatic unit for keeping in a thermostatic state while shaking and agitating a reaction liquid (a mixed liquid of specimen and reagents). Numeral 66 is an apparatus for aspirating and discharging liquid such as specimens. Numeral 90 is a holding part for holding reaction plates 12. The apparatus 66 for aspirating and discharging sample liquid and the holding part 90 are mounted on the same XY moving part 70, and are moved back and forth, to the right and left. Numeral 2 denotes an operation panel for setting and entering data. Numeral 4 is a printer, and 6 is a display unit.

The table 10 for holding the reaction plates 12 is partitioned by, for example, three partition members 30, so that four reaction plates are provided for. They are disposed from the nearest side (the lowest side in FIG. 4), first place 32a, second place 32b, third place 32c, and fourth place 32d. The first and second places 32a, 32b are the spaces for placing the reaction plates 12a, 12b before use. The third and fourth places 32c, 32d are spaces for placing the reaction plates after use, and are empty (open) before use. When the reaction plates 12a, 12b are used as the measurement starts, they are put in the places 32c, 32d.

Figure 5:
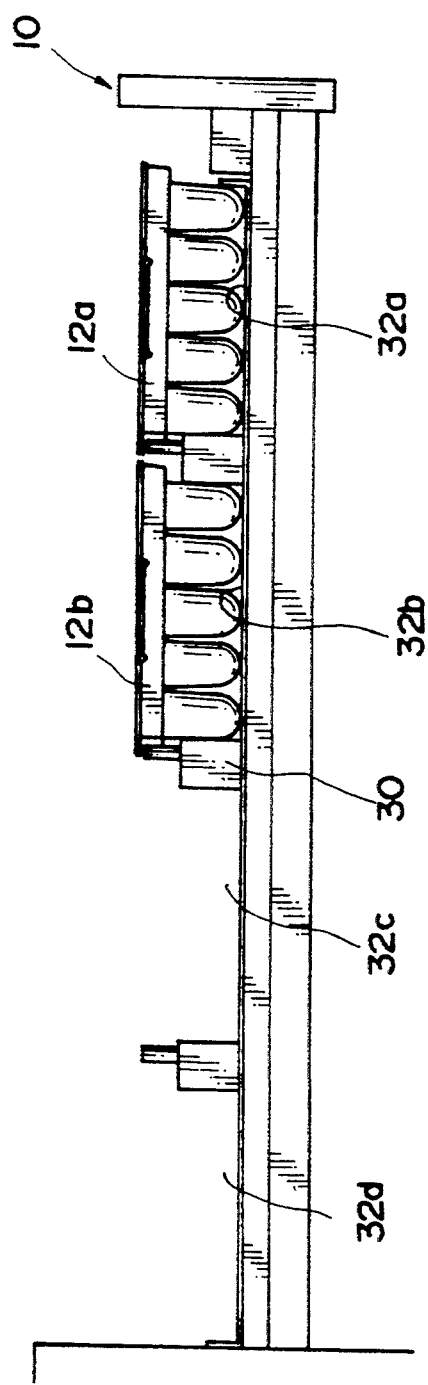
FIG. 5 is an explanatory diagram showing a drawn state of the table for a reaction plate as seen from the direction of arrow B in FIG. 4 (a side explanatory diagram around the table for reaction plate).

The table 10 can be drawn out in the direction of arrow A in FIG. 4. FIG. 5 is a view from the direction of arrow B in FIG. 4, showing the state of the table 10 being drawn out. By drawing out the table 10, the reaction plate can be placed and taken out easily.

On the specimen rack table 34, for example, up to eight specimen racks 36 can be mounted. One specimen rack can hold, for example, five specimen containers 38. The specimens are human serum, plasma or urine. Each specimen is aspirated and sampled through a penetration hole 42 of a chassis 40. The specimen rack table 34 can be also drawn out in the direction of arrow A, in the same manner as the reaction plate table 10.

Figure 6:
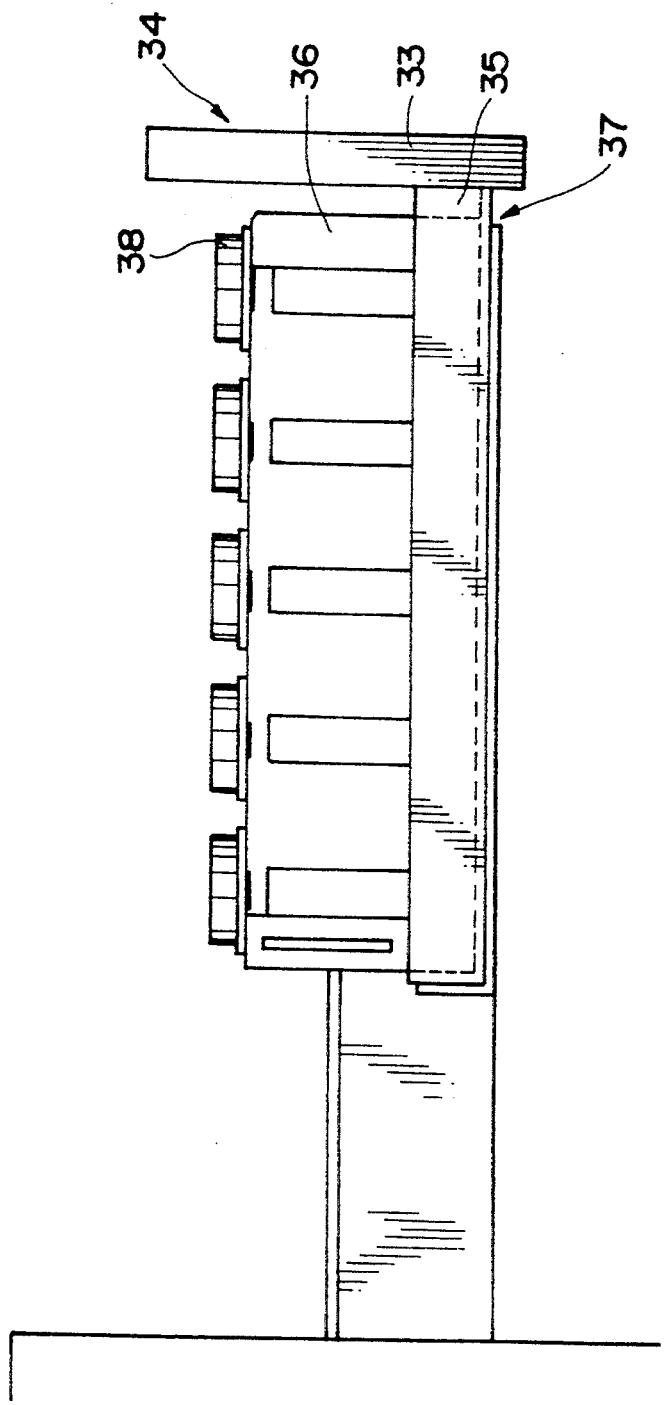
FIG. 6 is an shows a drawn state of the table for a specimen rack as seen from the direction of arrow B in FIG. 4 (a side explanatory diagram around the table for specimen rack).

FIG. 6 is a view from the direction of arrow B in FIG. 4, showing the state of the table 34 being drawn out. A mounting table 37 for a specimen rack comprising a front panel 33 and a bottom plate 35 can be detached. The specimen rack is placed or taken out by drawing out or removing the table 34. Usually, places for six racks on the left side are used, and the places for two racks on the right side are kept open for emergency specimens.

On the back side of the reagent thermostatic unit 44, a cooler (not shown) is provided, and the reagents are kept at about 15° C. or less. On the top of the reagent thermostatic unit 44, recesses 46, 48, 50 are provided, and buffer solution container 52, latex reagent container 54, and diluent liquid container 56 are put in the recesses.

The reaction plate 12 is put on the reaction thermostatic unit 58, and the reaction liquid which is a mixed liquid of specimen and reagents is kept around 45° C. by a heater (not shown) attached to the back side of the reaction thermostatic unit 58. Furthermore, the entire reaction thermostatic unit 58 imparts a shaking motion. The radius of rotation of the shaking motion is, for example, 1.5 mm, and the rotating speed is 600 rpm. On the top of the reaction thermostatic unit 58, there are a plurality of recesses 60 in which the container portions of the reaction plate settle. The reaction thermostatic unit 58 consists of a first place 58a and a second place 58b, and two reaction plates are put in these places, so that they can be kept thermostatically (in constant temperature), shaken and agitated simultaneously. Numerals 62, 64 are holding members for grasping and holding the reaction plate from both sides.

This automated immunochemical analyzer is provided with only one means for aspirating and discharging the liquid sample. The apparatus 66 for aspirating and discharging the sample liquid moves vertically for aspirating and discharging liquid. The apparatus 66 for aspirating and discharging sample liquid is furnished with the holding part 90 for holding and lifting the reaction plate 12.

The apparatus 66 for aspirating and discharging sample liquid provided with the holding part 90 is mounted on the XY moving part 70 which moves on the automated immunochemical analyzer two-dimensionally. Hence, the apparatus 66 for aspirating and discharging sample liquid can discharge the liquid aspirated at one position to another place, and can also move the reaction plate from one place to another place.

The actual operation is described below while referring to FIG. 4.

The apparatus 66 for aspirating and discharging sample liquid provided with the holding part 90 of the reaction plate moves to a position above the first place 32a on the table 10, where the holding part 90 descends, and the reaction plate 12a is held. After holding the reaction plate, it goes up, and moves to above the first reaction part 58a of the reaction thermostatic unit 58, and places the held reaction plate 12a. The reaction plate 12b is similarly moved from the second place 32b on the table 10 to above the second reaction part 58b.

Next, by the apparatus 66 for spirating and discharging sample liquid, the specimen, buffer solution and latex reagent are sequentially aspirated by specific volumes, and sequentially discharged into empty containers 14 of the reaction plate placed on the reaction thermostatic unit 58. For example, 100 μl of reaction liquid composed of 10 μl of specimen, 80 μl of buffer solution and 10 μl of latex reagent is held thermostatically and shaken and agitated, and the agglutination reaction of latex particles by the antigen-antibody reaction is promoted. Until a measurement is made, the reaction liquid is prepared for each specimen one after another. Numeral 116 is a cleaning tank for cleaning (rinsing) the pipet 82. If necessary, the specimen is preliminarily diluted by adding a diluent liquid.

When reaction for a specific time is over, the reaction liquid is sampled in the apparatus 66 for aspirating and discharging sample liquid, distributed in a measuring chamber 118, and is transferred to a measuring unit (not shown) and measured.

When all containers of the reaction plates are used up, the used reaction plates are moved to the places 32c, 32d on the table 10. Herein, the table 10 is drawn out, and the used reaction plates are discarded (dumped), and new reaction plates are put in places 32a, 32b. These placing and removing actions of reaction plates can be done also while the apparatus is in action. It is the same for placing and removing of specimen racks. Near the tables 10, 34, display means showing possible/impossible to draw out is provided, for example,the green lamp means (displays) possible and red lamp impossible, and according to the display the drawing action can be done. Even in an impossible state, by entering the draw-out reserve, it can be set in the possible state for drawing out by changing the sequence (however, the important sequence such as the reaction condition that may affect the result of measurement is not changed).

Figure 7:
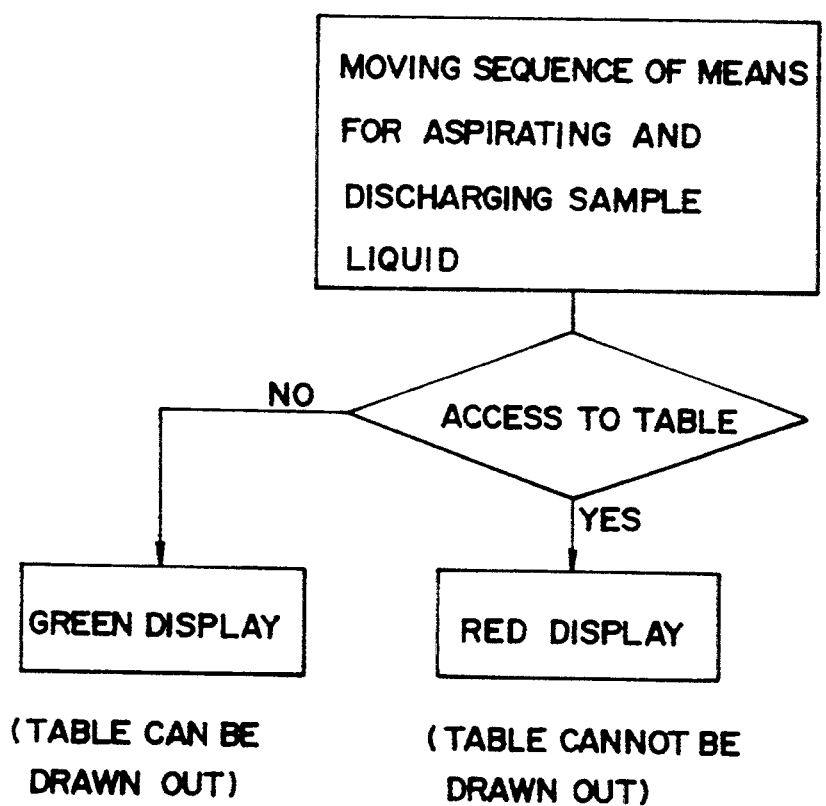
FIG. 7 is a flow chart showing a display method of display means.

FIG. 7 is a flow chart showing the display method of the display means. To display in the table for specimen rack, it is judged and displayed possible/impossible to draw out depending on whether the apparatus 66 for aspirating and discharging sample liquid moves to the table 34 for specimen rack or not. It is the same in the case of table 10 for the reaction plate.

Figure 8:
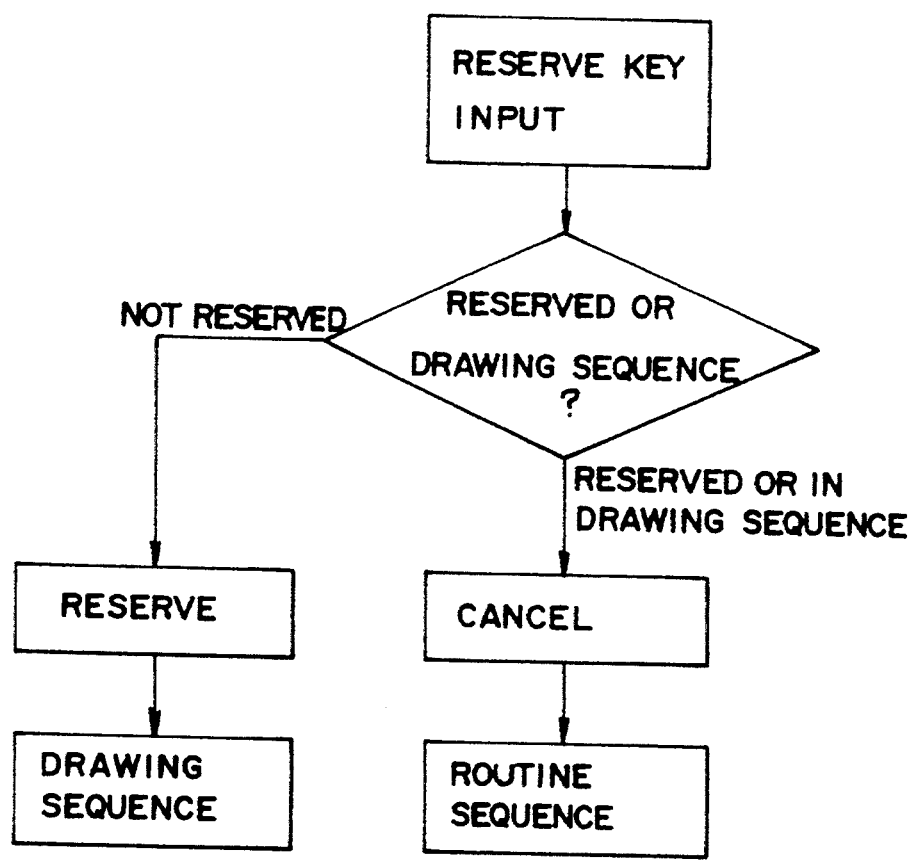
FIG. 8 is a flow chart showing reservation/cancellation of a draw-out table draw-out.

FIG. 8 is a flow chart showing the reserve/cancel fed drawing out a table. When reserved, the sequence for enabling draw out of the table is effected. That is, while continuing the reaction sequence or measurement sequence of specimens, the apparatus 66 for aspirating and discharging sample liquid is prevented from accessing the table. In the draw-out sequence, as shown in FIG. 7, the display turns to green, and it is ready to draw out. After closing, when the reserve key is entered again, the operation returns to the routine sequence.

Figure 9:
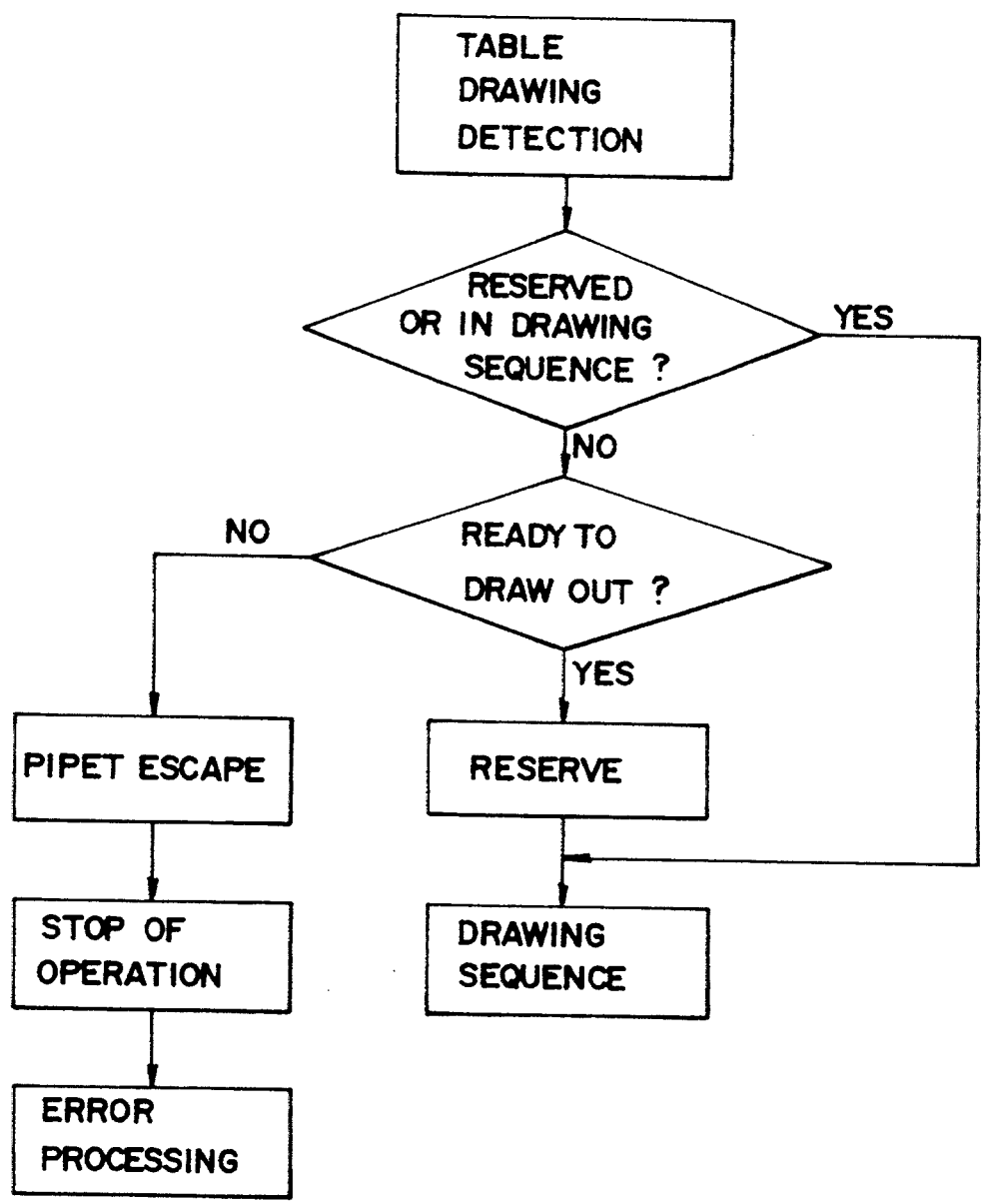
FIG. 9 is a flow chart showing the processing of a drawing table.

FIG. 9 is a flow chart showing the processing of drawing out the table. When already reserved or during the drawing out sequence, the drawing sequence starts or continues. If not reserved, when set in the drawing state, it is reserved. Not in the drawing state, together with an alarm, the pipet of the apparatus 66 for aspirating and discharging sample liquid is immediately lifted to escape, and stopped, and error processing is done (conducted).

It is more preferable to provide the apparatus with means for locking the table drawing out to actuate the locking means while the table drawing out is disabled so that the table cannot be drawn out.

Being thus constructed, the present invention brings about the following effect.

(1) Since the vertical movement of the pipet and the vertical movement of the reaction plate holding part can be done by one driving source, low cost and compact design are realized.

Having described preferred embodiments of the present invention with reference to the accompanying drawings, it is to be understood that the present invention is not limited to those precise embodiments, and that various changes and modifications may be effected therein by one skilled in the art without departing from the scope or the spirit of the invention as defined in the appended claims.

What is claimed is:

1. An apparatus for aspirating and discharging a liquid sample, said apparatus comprising:

a pipet for aspirating and discharging a liquid sample, an arm for holding the pipet, said pipet extending downwardly from said arm, arm guide means for guiding a movement of said arm in a vertical direction, a reaction plate holding part for holding a reaction plate formed in one body with a plurality of reaction containers, reaction plate holding part guide means for guiding a movement of the reaction plate holding part in the vertical direction, a pair of pulleys, a belt extending around the pulleys, having said arm attached to one side of said belt and said reaction plate holding part attached on the other side of said belt, and a driving source for rotating said belt vertically.

2. An apparatus for aspirating and discharging a liquid sample according to claim 1, said apparatus being connected to an XY moving part which is movable back and forth, and to the right and left.

* * * * *